United States Patent [19]

Wieser et al.

[11] Patent Number: 4,994,268

[45] Date of Patent: Feb. 19, 1991

[54] PHEROMONE FORMULATION FOR ATTRACTING SPRUCE BEETLES

[75] Inventors: Helmut Wieser; Elisabeth A. Dixon, both of Calgary; Herbert F. Cerezke, Edmonton; Alan, A. MacKenzie, Calgary, all of Canada

[73] Assignee: University of Calgary, Calgary, Canada

[21] Appl. No.: 269,426

[22] Filed: Nov. 10, 1988

[51] Int. Cl.$^5$ ............................................. A01N 25/00
[52] U.S. Cl. ....................................................... 424/84
[58] Field of Search ........................................... 424/84

[56] References Cited

U.S. PATENT DOCUMENTS 4,299,818 11/1981 Vité et al. ............................ 424/84
4,357,339 11/1982 Wilson et al. ....................... 514/403

OTHER PUBLICATIONS

The Merck Index Tenth Edition, p. 391, (1983).

Primary Examiner—Douglas W. Robinson
Assistant Examiner—Zohyeh A. Fay
Attorney, Agent, or Firm—Richard L. Neeley

[57] ABSTRACT

Novel compositions and methods for the attraction of spruce beetles *Dendroctonus rufipennis* are provided. The compositions are comprised of both insect and tree-produced semiochemicals alone or in combination to attract populations of spruce beetles. The compositions are effective for the attraction and manipulation of the spruce beetle populations.

10 Claims, No Drawings

PHEROMONE FORMULATION FOR ATTRACTING SPRUCE BEETLES

TECHNICAL FIELD

This invention relates to the management of insect pests, particularly to the use of semiochemicals as insect attractants.

BACKGROUND OF THE INVENTION

The spruce beetle, *Dendroctonus rufipennis*, is a species of bark beetle indigenous to North America, infesting all species of Picea. Normally present in relatively small numbers, spruce beetles are nonaggressive attackers, preferring weakened or downed material to healthy trees. However, under certain conditions, the tree killing potential of this forest pest can be devastating. Early detection of outbreaks associated with major stand disturbances is of the utmost importance in preventing high spruce mortality and commensurate volume losses. Traditional control methods are costly, both in manpower and equipment, and the benefits during extensive epidemics are localized and short-lived. Integrated pest management strategies using semiochemicals have been the subject of intense research, and are beginning to provide forest managers with new, effective tools for monitoring, trapping, and manipulating scolytid beetles.

Pheromones have shown variable success in manipulating certain Dendroctonus species. However, the response to pheromone formulations are species specific and must be determined on a species-to-species basis. For example, *D. ponderosae* has a different chemistry and responds to different semiochemicals than other species within the genus Dendroctonus. For this reason, attractants must be formulated individually for each particular species.

DESCRIPTION OF THE PRIOR ART

The extraction of frontalin from male *D. brevicomis* beetles is reported by Byers et al (1984) *Journal of Chemical Ecology* 10:861–877. Renwick and Hughes (1975) in *Insect Biochemistry* 5:495–463 obtained 3-methylcyclohex-2-enone (MCH) from *D. frontalis* exposed to vapors of 1-methylcyclohexene and concluded the bark beetles may have a general metabolic system for oxidation of hydrocarbons. In addition, the discovery of the occurrence of 1-methyl-2-cyclohexenol along with seudenol (3-methyl-2-cyclohexenol) in both *D. frontalis* and *D. pseudotsugae* by Renwick and Hughes (1975) supra suggested the existence of a general oxidation and rearrangement mechanism in these insects. Libbey et al (1983) *Journal of Chemical Ecology* 9:1533–1541 reported that on the basis of laboratory and field experiments, 1-methyl-2cyclohexenol is a female aggregation pheromone for *D. pseudotsugae*, attracting both sexes with males predominating. Frontalin used as the single component in polyethylene capillaries or capsules as tree baits to induce *D. rufipennis* attacks on living spruce was reported by Dyer and Chapman (1971) *Canada Department of Fisheries and Forestry Bi-Monthly Research Notes* 27:10–11, Dyer (1973) *Canadian Journal of Forest Research* 3:486–494, Dyer (1975) *Canadian Entomologist* 107:979–988 and Dyer and Lawko (1978) *Environment Canada Bi-Monthly Research Notes* 34:30–32. Dyer (1975) supra and Dyer et al (1975) *Journal of the Entomological Society of British Columbia* 72:20–22 report the use of a formulation of 1 part racemic frontalin and 2 parts of racemic alpha-pinene as tree baits for spruce in British Columbia. The use of seudenol with alpha-pinene to attract *D. rufipennis* to baited traps was reported by Furniss et al (1976) *Canadian Entomologist* 108:1297–1302 and Dyer and Lawko (1978) supra. Dyer and Lawko further disclose the use of seudenol as a tree bait on live spruce for *D. rufipennis*, and in traps where it favored males 1.6 to 1. Canadian patent No. 1,212,044 discloses a composition for attracting mountain pine beetles composed of exo-brevicomin, trans-verbenol and myrcene.

SUMMARY OF THE INVENTION

Chemical compositions and methods for the attraction of spruce beetles are provided. The compositions are comprised of 1-methyl-2-cyclohexenol in combination with either, or both, alpha-pinene and frontalin. The compositions are effective for the attraction and manipulation of spruce beetle populations.

DESCRIPTION OF THE SPECIFIC EMBODIMENTS

In accordance with the present invention, novel chemical compositions and methods for the attraction and manipulation of spruce beetles are provided. The method employs the use of chemical compositions which act as intraspecies attractants and anti-aggregants to manipulate significant numbers of spruce beetles. The compositions are provided at concentrations which provide combinations inducing the greatest beetle response.

Chemical compositions include semiochemicals and other message-bearing chemicals which attract or enhance the attraction of beetles. For the purposes of the present invention, semiochemicals include both the pheromones which are produced by beetles to induce other beetles of the same species to aggregate on a particular host tree, and tree-produced synergists which act with one or more aggregation pheromone to intensify the chemical message.

Pheromones are a group of organic compounds produced by insects which function as communication means and as sex attractants. Those pheromones which function to attract spruce beetles include both male and female aggregation pheromones such as frontalin (1,5-dimethyl-6,8-dioxabicyclo[3.2.1]octane), seudenol (3-methyl-2-cyclohexenol), 1-methyl-2-cyclohexenol and the like. These compounds can be used alone or in combination with each other to elicit beetle response. Although other pheromones may be utilized for attracting spruce beetles, the importance of 1-methyl-2-cyclohexenol as an effective synergist for spruce beetles has not been realized before. 1-Methyl-2-cyclohexenol is a female aggregation pheromone which attracts both sexes of beetles, with females responding more than males. Although MCOL is an effective attractant when used alone, beetle response can be enhanced by the addition of either frontalin or tree-produced synergists. An enhanced response is achieved when MCOL, frontalin, and tree-produced synergists are utilized together. Thus, superior beetle responses are found with a chemical composition containing all three compounds.

Tree-produced synergists generally include a number of terpenes and terpenoids. These compounds act synergistically with the aggregation pheromones to intensify the chemical message. The terpene synergists utilized in the present invention may be either acyclic or cyclic with one or more rings. These include alphapines, beta-pinene, myrcene, beta-phellandrene, delta-3-carene, and the like. Other derivatives which may find use as camphor, menthol, terpineol, borneol, geraniol, bornyl acetate, and the like. Although alpha-pinene has been demonstrated to elicit superior beetle response when utilized with MCOL and frontalin, the other semiochemicals may be substituted for use in the chemical composition.

The semiochemicals for beetle attraction occur in nature and have been isolated. They may also be synthesized by chemical methods as outlined in the experimental section. Isolation or chemical synthesis of the compounds may result in racemic mixtures which serve as effective aggregants for beetle populations. Thus, for purposes of the present invention, racemic mixtures or the individual isomers of the semiochemicals find use in chemical compositions.

The attractants or semiochemicals are provided at concentrations to effectively attract beetle populations. The concentration of the attractants are defined by their release rates. In the utilization of MCOL, frontalin, and alpha-pinene, baited trap experiments have shown release rates of about 0.5 to about 5 mg/24 hours for MCOL, about 10 to about 100 mg/24 hours for alpha-pinene, and about 0.05 to about 5 mg/24 hours for frontalin, to be effective. Where other semiochemicals are substituted, they are provided at concentrations in a range of about 1 to 100 mg/24 hrs.

Chemical compositions may be used to trap, monitor, or suppress the beetle population. They are highly effective in inducing attack by natural populations of spruce beetles on baited spruce trees. They can be used to attract beetles to designated trap-trees after which the trees may be harvested or treated with insecticides. Thus, the chemical compositions can be used with any other methods for controlling insect populations.

Manipulation of spruce beetles includes attracting spruce beetles to living spruce trees and inducing the beetles to mass attack or infest the tree. The method entails exposing the beetles to trees baited with the chemical compositions as discussed above in amounts which are effective in causing the beetles to mass attack the baited trees and nearby trees. An aspect of this embodiment provides for concentrating spruce beetle infestations in selected areas of a forest. Using this method, it is also possible to move the locus of spruce beetle infestation within a forest from one location to another. This involves exposing the beetles to the chemical compositions in a combined amount which is effective in moving the beetles. The beetles can be concentrated in a particular area of the forest or moved from one area to another area within the forest so that the beetles are concentrated in an area for logging, for treatment of the trees with insecticide, or for other means for eradicating the beetles. Further, it may be useful to contain the spruce beetle infestations within a previously attacked area of a forest, thus protecting the unattacked trees.

As disclosed above, the invention provides methods for attracting spruce beetles to traps for the purposes of monitoring or suppressing beetle populations. One embodiment entails exposing the beetles to a trap baited with the chemical composition of the present invention in an amount which is effective in causing the beetles to be captured in or on the trap.

The traps utilized with the present invention may be any insect trap which can be baited with the chemical composition. Lindgren funnel traps are particularly useful as they can be baited with the aggregants and suspended from nonhost trees with polyethylene cords. The chemical compositions may be placed inside microcentrifuge tubes, capillaries or appropriately encapsulated devices and wired within the trap funnels. The compositions may also be used with any tree baiting device. Tree baiting devices have found use wherein containers were mounted in a plastic cradle and held in position against the bole of host trees by nylon straps, staples or nails.

A simple device which may be used to secure or mount the above described attractants to the bole of live standing trees or on downed trees or logs is a bait cradle which is formed in the shape of a "Z" with one end forming a hook, which when supported from beneath by a nylon strap, will hold the baited device securely in place. The other end of the cradle, formed inward towards the tree, serves as a platform for supporting the release devices. Predrilled holes in this portion of the device accommodate the microcentrifuge (MCF) tubes filled with the attractant chemicals.

The following experiments are offered by way of illustration and not by way of limitation.

EXPERIMENTAL

Example 1

Chemical Synthesis of MCOL

A solution of 2-cyclohexenone (Aldrich, 97%; 13 gm, 0.135 mol) in dry ether (130 ml) was added dropwise to an ethereal solution of methyllithium (1.3 M, 330 ml, 0.447 mol) under $N_2$ at $-78°$ C. The reaction mixture was stirred at room temperature overnight and then added to ice water. The ether layer was separated and the aqueous layer was extracted with ether ($3 \times 100$ ml). The combined ether extracts were dried (anhydrous $MgSO_4$) and the solvent was distilled using a 12" Vigreux column. Distillation of the residue gave 12.9 gm (85%) of 1-methyl-2-cyclohexenol.

Example 2

Chemical Synthesis of Frontalin

Preparation of 2-carbomethoxy-2,6-dimethyl-3,4-dihydro-2 H-pyran

A mixture of methyl vinyl ketone (126 gm, 1.8 mol) and methyl methacrylate (180 gm, 1.8 mol) in benzene (200 ml) was heated for 2 hours at 200° C in an autoclave. After evaporation of the solvent the residue was distilled through a 40 cm Vigreux column to give 50 gm of a mixture composed of 71% of 2-carbomethoxy-2,6-dimethyl-3,4-dihydro-2H-pyran and 26% of methyl vinyl ketone dimer. Separation of the dimer was achieved by flash chromatography (10% ether in pentane), with quantitative recovery of the ester, 2-carbomethoxy-2,6-dimethyl-3,4-dihydro-2 H-pyran.

Preparation of frontalin

A solution of 2-carbomethoxy-2,6-dimethyl-3,4-dihydro-2 H-pyran (11.2 gm, 0.066 mol) in dry ether was added dropwise with stirring to lithium aluminum hydride (3 gm, 0.079 mol) in dry ether. The reaction mixture was heated under reflux for 4 hours, cooled and decomposed with water (3 ml), aqueous 15% NaOH solution (3 ml) and finally water (9 ml). It was stirred at room temperature for 2 hours and filtered. The ether solution containing the resulting alcohol was treated with a catalytic amount of p-toluenesulfonic acid, stirred at room temperature for 2 hours and neutralized with K$_2$CO$_3$. The solvent was removed using a 40 cm Vigreux column and the residue was distilled to give 7.6 gm (75.6%) of frontalin.

Example 3

Baited Trap Experiments

In two trapping experiments, 70 Lindgren funnel traps (Phero Tech, Inc.) were baited with the aggregants listed in Table 1 below, representing 7 replications of 5 different bait formulations per experiment. Baited traps were suspended from polyethylene cords tied to nonhost trees. The pheromone chemicals were dispensed at the desired predetermined rates from microcentrifuge tubes or capillaries, as appropriate, wired within the trap funnels (chemicals and release rates are listed in the table below). All traps were monitored weekly and the captured spruce beetles collected, counted, placed in storage bottles and sent to the entomology laboratory at the Northern Forest Research Centre, Canadian Forestry Service, Edmonton, Alberta, for formal identification, sexing, sizing, and final tally.

TABLE 1

| BAIT FORMU-LATION | BAIT CHEMICALS | RELEASE RATES[1] (mg/24 hrs) | | |
|---|---|---|---|---|
| | | a | b | c |
| A | αpinene plus seudenol | 33 | 1.7 | |
| B | αpinene plus MCOL | 33 | 1.6 | |
| C | αpinene plus frontalin | 33 | | 0.048 |
| D | αpinene plus frontalin | 33 | | 0.14 |
| E | αpinene plus frontalin | 33 | | 0.50 |
| F | A plus frontalin | 33 | 1.7 | 0.048 |
| G | A plus frontalin | 33 | 1.7 | 0.14 |
| H | A plus frontalin | 33 | 1.7 | 0.50 |
| J | B plus frontalin | 33 | 1.6 | 0.048 |
| K | B plus frontalin | 33 | 1.6 | 0.14 |
| L | B plus frontalin | 33 | 1.6 | 0.50 |

[1]The letters a, b, and c under release rates refer to the first, second, and third components of each formulation, respectively.

Bait formulation K, containing sufficient amounts of racemic alpha-pinene plus MCOL and frontalin at the release rates stated in Table 1, attracted significantly more *D. rufipennis* beetles to baited traps than any of the other formulations tried. Baits containing binary combinations of racemic alpha-pinene plus frontalin are more attractive to female *D. rufipennis* beetles than male beetles, whereas the reverse appears to be true when seudenol is added to this combinantion. Almost equal numbers of each sex of beetles are attracted by baits containing alpha-pinene plus frontalin at high frontalin release rates, and baits containing alpha-pinene plus MCOL and frontalin. Thus, when a funnel trap is baited for use in field conditions, the latter bait formulation will generally be preferable to obtain maximum attraction for both mal and female beetles.

Example 4

Tree Baiting Experiments

The tree baits used were intended to parallel those in the baited trap experiments. In two experiments, 66 live spruce trees were baited representing 6 replicates of 5 formulations and 6 replicates of 6 formulations, respectively. Release devices similar to those in the trapping experiments were used to dispense the pheromones. The containers were mounted in plastic cradles and held in position against the bole of host trees by nylon straps.

At the end of the season, each baited tree was surveyed for successful and unsuccessful attacks, by exfoliating a 1-meter wide circumferential band straddling the bait holder. Complete counts of beetle entries were made within this band, from which attack densities were derived.

Combinations of semiochemicals containing frontalin at release rates of 0.14 mg/24 hrs (bait formulations D, G, and K) attracted consistently fewer beetles to baited spruce trees than comparable baits with low and high frontalin release rates. In the binary formulas, low and high release rates of frontalin induced similar attack densities. However, in the ternary formulations containing frontalin, the higher release rates induced substantially greater attack densities. Thus, when a tree is baited for the purpose of manipulating *D. rufipennis* populations in the field, the ternary bait formulation of racemic alpha-pinene plus MCOL and frontalin at the higher release rate of 0.50 mg/24 hrs will generally be preferable to obtain maximum attraction for female beetles.

All of the above bioassays were conducted utilizing MCOL and frontalin obtained by the chemical syntheses described above. The racemic alpha-pinene utilized was purchased commercially and employed without further purification.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of trapping and tree baiting spruce beetles by applying a chemical composition comprising 1-methyl-2-cyclohexenol in a concentration which is effective to attract said beetles and a spruce beetle attracting enhancing amount of at least one of frontalin and tree-produced semiochemicals to a region frequented by spruce beetles.

2. A method, according to claim 1 wherein said tree-produced semiochemical is alpha-pinene, myrcene, beta-pinene, beta-phellandrene, delta-3-carene, camphor, or bornyl acetate.

3. A method, according to claim 1, wherein said chemical composition comprises 1-methyl-2-cyclohexenol and frontalin.

4. A method, according to claim 3, wherein said chemical composition further comprises alpha-pinene.

5. A method, according to claim 4, wherein the concentration of semiochemicals is defined by release rates which are in the range of about 0.5 to 5 mg/24 hours for 1-methyl-2-cyclohexenol, about 0.05 to 5 mg/24 hours for frontalin, and about 10 to 100 mg/24 hours for alpha-pinene.

6. A method for controlling spruce beetle populations by applying a chemical composition comprising 1-methyl-2-cyclohexenol to an area of a forest away from spruce beetle infestation in a concentration which is effective to move said population from one area of a forest to another designated area.

7. A method, according to claim 6, wherein said chemical composition further comprises frontalin.

8. A method, according to claim 6, wherein said chemical composition further comprises alpha-pinene.

9. A method, according to claim 6, wherein said chemical composition further comprises frontalin and alpha-pinene.

10. A method, according to claim 9, wherein said concentration is defined by release rates which are in the range of about 0.5 to 5 mg/24 hours for 1-methyl-2-cyclohexenol, about 0.05 to 5 mg/24 hours for frontalin, and about 10 to 100 mg/24 hours for alpha-pinene.

* * * * *